United States Patent
Peter et al.

(10) Patent No.: US 11,717,633 B2
(45) Date of Patent: Aug. 8, 2023

(54) PROCESS, COMPUTER PROGRAM, DEVICE AND VENTILATION SYSTEM FOR THE DETECTION OF A LEAK IN A PATIENT GAS MODULE

(71) Applicant: Drägerwerk AG & Co. KGaA, Lübeck (DE)

(72) Inventors: Gerd Peter, Lübeck (DE); Uwe Schmid, Lübeck (DE); Christoph Osterloh, Klempau (DE)

(73) Assignee: Drägerwerk AG & Co. KGaA, Lübeck (DE)

(*) Notice: Subject to any disclaimer, the term of this patent is extended or adjusted under 35 U.S.C. 154(b) by 374 days.

(21) Appl. No.: 16/771,632

(22) PCT Filed: Dec. 12, 2018

(86) PCT No.: PCT/EP2018/084444
§ 371 (c)(1),
(2) Date: Jun. 10, 2020

(87) PCT Pub. No.: WO2019/115571
PCT Pub. Date: Jun. 20, 2019

(65) Prior Publication Data
US 2020/0353197 A1     Nov. 12, 2020

(30) Foreign Application Priority Data
Dec. 15, 2017  (DE) .................. 10 2017 011 625.3

(51) Int. Cl.
*A61M 16/00* (2006.01)
*A61M 16/08* (2006.01)
(Continued)

(52) U.S. Cl.
CPC ......... *A61M 16/085* (2014.02); *A61B 5/0836* (2013.01); *A61M 16/0066* (2013.01);
(Continued)

(58) Field of Classification Search
CPC ................ A61M 16/085; A61M 16/00; A61M 2016/0027; A61M 2016/1025;
(Continued)

(56) References Cited

U.S. PATENT DOCUMENTS

| 5,335,653 A | 8/1994 | Blomqvist et al. |
| 8,033,280 B2 | 10/2011 | Heinonen |

(Continued)

FOREIGN PATENT DOCUMENTS

| CA | 2941761 A1 | 11/2015 |
| CN | 103180002 A | 6/2013 |

(Continued)

OTHER PUBLICATIONS http://www.cybis.se/wiki/index.php/Correlation_analysis. (Year: 2012).*
(Continued)

*Primary Examiner* — Philip R Wiest
*Assistant Examiner* — Sarah B Lederer
(74) *Attorney, Agent, or Firm* — McGlew and Tuttle, P.C.

(57) ABSTRACT

A process (10), with a computer program, a device (30) and a ventilation system (40) detect a leak in a patient gas module, which suctions and analyzes a continuous sample gas stream from a ventilated patient (20), in a ventilation system for ventilating a patient (20). The process includes a determination (12) of a first time curve of a carbon dioxide concentration in a breathing gas mixture of the patient (20) and the determination (14) of a second time curve of a concentration of another gas in the breathing gas mixture, which gas is different from carbon dioxide. The process (10) further includes a determination (16) of a statistical similarity indicator between the first time curve and the second time curve and the detection (18) of the leak based on the similarity indicator.

20 Claims, 8 Drawing Sheets

(51) Int. Cl.
    *A61B 5/083*  (2006.01)
    *A61M 16/20* (2006.01)
    *A61M 16/22* (2006.01)
    *A61M 16/10* (2006.01)

(52) U.S. Cl.
    CPC ..... *A61M 16/0808* (2013.01); *A61M 16/0833* (2014.02); *A61M 16/208* (2013.01); *A61M 16/22* (2013.01); *A61M 2016/0027* (2013.01); *A61M 2016/103* (2013.01); *A61M 2016/1025* (2013.01); *A61M 2016/1035* (2013.01); *A61M 2202/0208* (2013.01); *A61M 2202/0225* (2013.01); *A61M 2202/0241* (2013.01); *A61M 2202/0283* (2013.01); *A61M 2205/15* (2013.01); *A61M 2205/52* (2013.01)

(58) Field of Classification Search
    CPC .... A61M 2016/103; A61M 2016/1035; A61M 2205/52; A61B 5/0836
    See application file for complete search history.

(56) References Cited

U.S. PATENT DOCUMENTS

2008/0202526 A1* 8/2008 Heinonen ............ A61M 16/01
                                                    128/204.22
2010/0139659 A1* 6/2010 von Blumenthal ..................
                                                    A61M 16/0051
                                                    128/204.23
2011/0196251 A1  8/2011 Jourdain et al.
2015/0273172 A1* 10/2015 Pessala ............. A61M 16/0069
                                                    128/203.12
2017/0016799 A1  1/2017 Zitting

FOREIGN PATENT DOCUMENTS

| | | |
|---|---|---|
| CN | 103379856 A | 10/2013 |
| DE | 4103868 B4 | 5/2005 |
| EP | 1961439 A1 | 8/2008 |
| EP | 1974763 A1 | 10/2008 |
| WO | 2004/076944 A2 | 9/2004 |
| WO | 2012085753 A1 | 6/2012 |
| WO | 2014/068000 A1 | 5/2014 |

OTHER PUBLICATIONS

End-Tidal Co2 Excretion Waveform and Error With Gas Sampling Line Leak. Joanne Zupan, et al. pp. 579-581.

* cited by examiner

PROCESS, COMPUTER PROGRAM, DEVICE AND VENTILATION SYSTEM FOR THE DETECTION OF A LEAK IN A PATIENT GAS MODULE

CROSS REFERENCE TO RELATED APPLICATIONS

This application is a United States National Phase Application of International Application PCT/EP2018/084444, filed Dec. 12, 2018, and claims the benefit of priority under 35 U.S.C. § 119 of German Application 10 2017 011 625.3, filed Dec. 15, 2017, the entire contents of which are incorporated herein by reference.

TECHNICAL FIELD

Exemplary embodiments pertain to a process, to a computer program, to a device and to a ventilation system for the detection of a leak in a patient gas module, especially but not exclusively, to a concept for the detection of leaks based on a comparison of concentration curves of different gases in a breathing gas mixture in a patient gas module or ventilation system

TECHNICAL BACKGROUND

Mechanically ventilating patients is known from the field of conventional technology. In this case, a ventilation gas is fed to the patient in a phase of inhalation and discharged again in a phase of exhalation. Various parameters of the breathing gas can be monitored in this connection, and, for example, so-called patient gas modules are used for gas analysis. E.g., a part of the gas can in each case be suctioned in order to feed it to a gas analysis in a patient module.

Diluting effects due to penetrating ambient air, which lead to gas concentration measurement errors, cause leaks on the suction section (e.g., via a sample gas line, water trap and aas monitor-internal tubing up to the gas-measuring cell) during the suctioning patient gas measurement, which suctions a continuous gas stream from the patient via a sample gas line. This is especially problematic in case of anesthesia work areas, which are equipped with closed loops. The measured concentration values (potentially subject to the aforementioned errors) are used here to control the dispensing of gas. If measuring errors occur here that are not discovered, then there will be errors in dispensing, which may lead, among other things, even to a patient injury.

The document U.S. Pat. No. 8,033,280 B2 describes a process for the determination of a leak in the sample gas line by the concentrations of at least two gases being measured and simultaneous changes of these concentrations in the direction of known ambient gas concentrations being identified. These changes are then interpreted as a leak. The two gases are ideally carbon dioxide CO2 and oxygen O2. This monitoring measures relatively and determines the change in concentration between the current breathing phase and the previous breathing phase. If the leak occurs abruptly between two breathing phases with a diluting effect of sufficient magnitude, this can thus be detected. Slowly developing leaks can be detected only with difficulty.

The document WO 2014/068000 A1 pertains to the detection of leaks by a pressure measurement in a patient monitor and comparison with a pressure measurement in a circulation system. In this case, it is possible that changes in the resistances of the sample gas line/water trap will overlap the effect of the airway pressure changes in the patient monitor. Changes in pressure can be highly attenuated when the pump is running and possibly lead to a meaningful monitoring only for sufficiently high air way pressure set values. This principle with two distributed sensors is followed in the document WO 2004/076944 A2.

SUMMARY

Therefore, there is a need to provide an improved concept for the detection of a leak in a ventilation system for ventilating a patient. Exemplary embodiments of a process, of a computer program, of a device and of a process according to the invention meet this need.

Exemplary embodiments are based on the discovery that it is possible to measure a plurality of gas concentrations in a gas mixture of a ventilator. The time curves of the gas concentrations are influenced differently in case of a leak, so that concentration time curves may form the basis of a leak detection. In addition, exemplary embodiments are based on the discovery that the curve of a carbon dioxide concentration in a breathing gas mixture of a patient may form a reference for comparison with a concentration curve of another gas in the breathing gas mixture of the patient.

Therefore, exemplary embodiments provide a process, which suctions and analyzes a continuous sample gas stream from a ventilated patient, for the detection of a leak in a patient aas module, for example, even in a ventilation system for ventilating a patient with a ventilation gas mixture. For example, a measurement error of up to 20% in the gas concentration measurement is caused due to the leak of, e.g., 40 mL/min (in case of a suctioned sample gas flow of 200 mL/min), while it is completely irrelevant for the ventilation of a patient with a respiratory minute volume of ca. 8 L. The process comprises the determination of a first time curve of a carbon dioxide concentration in a breathing gas mixture of the patient and the determination of a second time curve of a concentration of another gas in the breathing gas mixture, which gas is different from carbon dioxide. The process further comprises the determination of a statistical similarity indicator between the first time curve and the second time curve and the detection of the leak based on the similarity indicator. Exemplary embodiments may thus provide a reliable detection of a leak. In this case, the other gas may be, for example, oxygen, nitrous oxide or an anesthetic gas.

In some exemplary embodiments, the similarity indicator corresponds to a phase shift between the first curve and the second curve. Exemplary embodiments may thus make possible a robust detection of a leak. The determination of the similarity indicator may comprise the determination of a deformation in the first curve or in the second curve, which deformation is peculiar to a leak. In some exemplary embodiments, the similarity indicator may be an indicator of a symmetry between the first curve and the second curve. The similarity indicator may be a covariance between the first time curve and the second time curve of the concentrations. At least some exemplary embodiments may thus use a statistical analysis to detect a leak. In other exemplary embodiments, the similarity indicator may be a covariance between a first time curve and a second time curve of concentration changes.

In some exemplary embodiments, the comparison of the similarity indicator with a threshold value and the detection of the leak based on the threshold value comparison may be carried out. Thus, exemplary embodiments may make possible a cost-effective signal processing. In addition, a calibration of the threshold value based on a reference measurement at the ventilation system without leak may be carried out in some exemplary embodiments. The reliability of the process can thus be increased even further. The determination of a run time of the breathing gas mixture from the patient via a sample gas line to a patient gas module may, in addition, be carried out in some exemplary embodiments. The run time may also be taken into consideration in case of the detection of a leak. In this respect, exemplary embodiments may comprise the determination of a run time of concentration changes in the breathing gas mixture and the determination of the similarity indicator based on the run times.

The determination of the run tune may be based on concentration changes over time and/or based on an analysis of concentration changes before and after a beginning of breathing phases. In some other exemplary embodiments, the process may further comprise the carrying out of a pressure measurement at the ventilation system when a leak was detected. The measurement of pressure in exemplary embodiments may be taken into consideration in the detection of leaks or even in the location of a leak.

Another exemplary embodiment is a computer program with a program code for carrying out one of the processes described herein when the program code is executed on a computer, on a processor or on a programmable hardware component. Other exemplary embodiments are a device for carrying out one of the processes described herein and a ventilation system for a patient with such a device.

Other advantageous configurations are described in more detail below on the basis of the exemplary embodiments which are shown in the drawings and to which exemplary embodiments are, however, not all generally limited. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
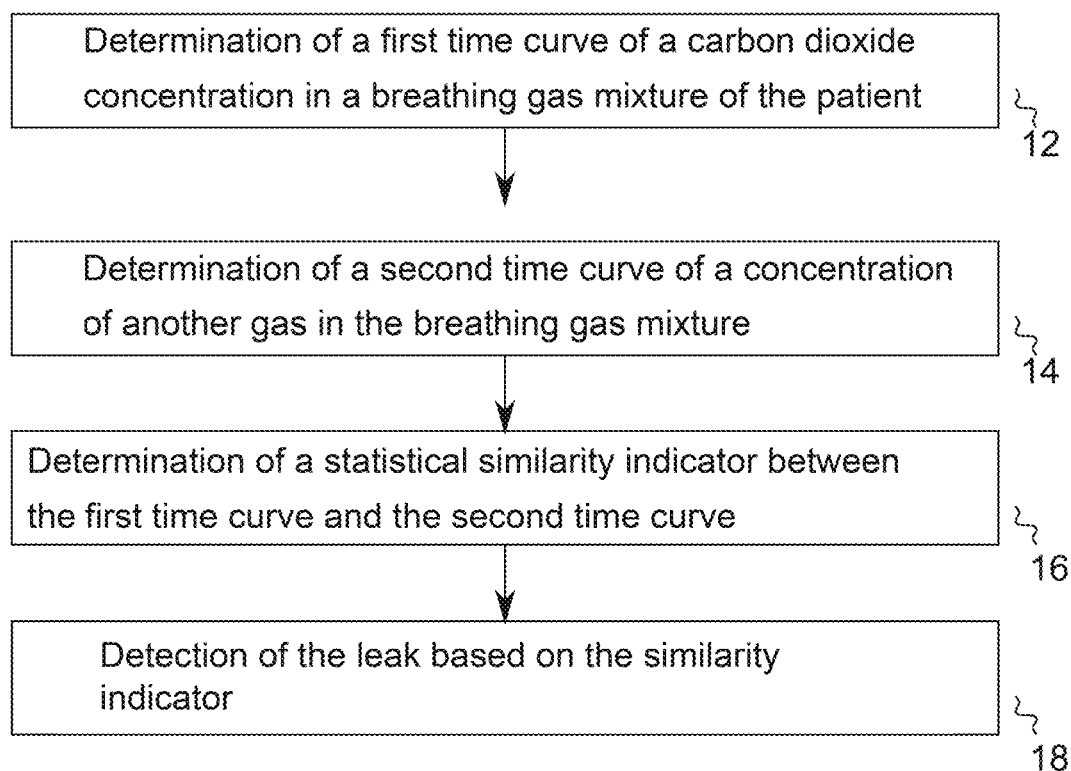
FIG. 1 is a flow chart of an exemplary embodiment of a process for the detection of a leak in a ventilation system for ventilating a patient.

Referring to the drawings, different exemplary embodiments will now be described in detail with reference to the attached drawings, in which some exemplary embodiments are shown.

In the following description of the attached figures, which show only some examples of exemplary embodiments, identical reference numbers may designate identical or comparable components. Further, summary reference numbers may be used for components and objects that occur as multiple components or objects in an exemplary embodiment or in a drawing, but are described together concerning one or more features. Components or objects that are described with identical or summary reference numbers may have an identical configuration but possibly also different configurations concerning individual features, a plurality of features or all features, for example, their dimensions, unless something else explicitly or implicitly appears from the description. Optional components are represented by broken lines or arrows in the figures.

Even though exemplary embodiments may be modified and changed in different ways, exemplary embodiments are shown in the figures as examples and will be described herein in detail. It should, however, be made clear that it is not intended to limit exemplary embodiments to the particular fo is disclosed, but exemplary embodiments shall rather cover all functional and/or structural modifications, equivalents and alternatives, which are within the scope of the present invention. Identical reference numbers designate identical or similar components in the entire description of the figures.

It should be noted that an element that is described as being "connected" or "coupled" with another element may be connected or coupled directly with the other element or that elements located in between may be present. If, by contrast, an element is described as being "directly connected" or "directly coupled" with another element, no elements located in between are present. Other terms that are used to describe the relationship between elements should be interpreted in a similar manner (e.g., "between" versus "directly in between," "adjoining" versus "directly adjoining," etc.).

The terminology that is being used here is used only to describe certain exemplary embodiments and shall not limit the exemplary embodiments. As being used herein, the singular forms "a," "an" and "the" shall also include the plural forms, unless something else unambiguously appears from the context. It should further be made clear that the terms such as, for example, "contains," "containing," "has," "comprises," "comprising" and/or "having," as being used herein, indicate the presence of said features, integers, steps, work processes, elements and/or components, but they do not rule out the presence or the addition of one or more features, integers, steps, work processes, elements, components and/or groups thereof.

Unless defined otherwise, all the terms being used herein (including technical and scientific terms) have the same meaning that a person having ordinary skill in the art in the field to which the exemplary embodiment belongs attributes to them. It should further be made clear that terms, e.g., those that are defined in generally used dictionaries, are to be interpreted as if they had the meaning that is consistent with their meaning in the context of the pertinent technique, rather than in an idealized or excessively formal sense, unless this is expressly defined here.

FIG. 1 shows a flow chart of an exemplary embodiment of a process 10, which suctions and analyzes a continuous sample gas stream from a ventilated patient, for the detection of a leak in a patient gas module, for example, in a ventilation system for ventilating a patient. The process 10 comprises the determination 12 of a first time curve of a carbon dioxide concentration in a breathing gas mixture of the patient and the determination 14 of a second time curve of a concentration of another gas in the breathing gas mixture, which gas is different from carbon dioxide. The process further comprises the determination 16 of a statistical similarity indicator between the first time curve and the second time curve and the detection 18 of the leak based on the similarity indicator.

Figure 2:
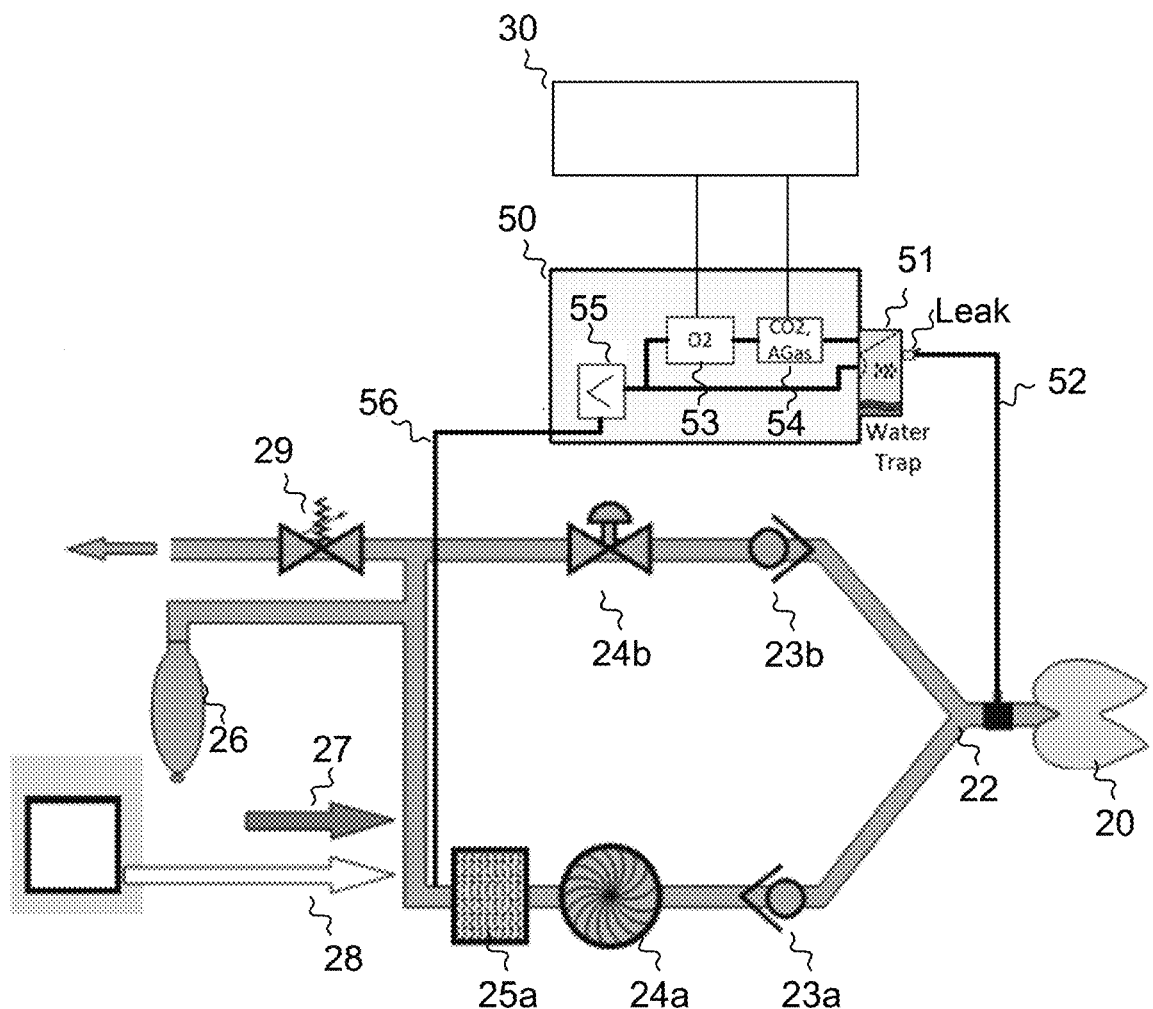
FIG. 2 is a schematic view showing a ventilation system for ventilating a patient in an exemplary embodiment.

FIG. 2 shows a ventilation system 40 for ventilating a patient 20 in an exemplary embodiment. The patient 20 is connected to two branches for the feed (inhalation) and discharge (exhalation) of the breathing gas via a mouthpiece and a branch piece or even a Y-piece 22. A nonreturn valve 23a, which lets gas through in the direction of the patient 20 and blocks it in the opposite direction, is located in the lower branch, which is provided for the feed. A blower 24a ensures a corresponding volume flow in the direction of the patient 20. A carbon dioxide absorber 25a that absorbs carbon dioxide from the fed breathing gas mixture is arranged upstream of the blower 24a. A nonreturn valve 23b, which lets through breathing gas in the direction away from the patient 20 and blocks it in the direction towards the patient 20, is also located in the upper branch of the ventilation system 40, which is provided for the discharge of the breathing gas. The nonreturn valve 23b is followed by a PEEP valve 24b (from English positive end-expiratory pressure). Together with the blower, the PEEP valve 24b ensures a controllable positive pressure in the lungs of the patient 20 during the phase of inhalation and opens or maintains a selectable residual pressure during the phase of exhalation. The upper branch and the lower branch of the ventilation system 40 may be connected via a T-piece, which is further connected to a breathing bag 26, via which the ventilation circuit can be driven. In addition, fresh air/fresh gas 27 and/or vaporous anesthetic 28 can be fed to the circuit.

As FIG. 2 further shows, the ventilation system 40 can be connected via another valve 29 to other components, for example, for the purification of the breathing gas. The valve 29 may be an APL (from English adjustable pressure-limiting) valve, which can make possible, on the one hand, a pressure limitation in case of volume-controlled ventilation and, on the other hand, the spontaneous breathing of the patient. The valve 29 opens when the set maximum pressure is reached.

FIG. 2 further illustrates an exemplary embodiment of a device 30 for carrying out one of the processes 10 described herein, which device is coupled to a patient gas module 50. The patient gas module 50 is coupled with the ventilation system 40 via a water trap 51, for the separation of condensation water and impurities, and a tube 52. A leak may occur, for example, at this tube or at the connection thereof to the water trap 51. Gas concentrations are determined 53, 54 in the patient gas module 50, and a pump 55 delivers the gas via a return tube 56 back into the system in the present exemplary embodiment. According to FIG. 1, a carbon dioxide concentration (CO2) is determined in the present exemplary embodiment and at least one concentration of another gas. The other gas may be, for example, oxygen (O2), nitrous oxide (N2O) or an anesthetic gas (Agas).

The concentrations are then provided to the device 30 and processed according to the process 10 of FIG. 1. Another exemplary embodiment is a computer program with a program code for carrying out one of the processes described herein when the program code is executed on a computer, on a processor or on a programmable hardware component. The device 30 may be implemented in this respect as a computer, a processor or a programmable hardware component. The device may correspond to any desired controller or processor or to a programmable hardware component in the exemplary embodiments. In this respect, the device may be implemented as programmable hardware with correspondingly adapted software. In this case, any desired processors, such as Digital Signal Processors (DSPs) can be used. Exemplary embodiments are not limited in this case to a certain type of processor. Any desired processors or even a plurality of processors are conceivable for the implementation of the device 30.

The device 30 can accordingly be configured for the processing of scanned values of the individual concentrations. In exemplary embodiments, the concentrations are correspondingly scanned, and the scanning rate is selected correspondingly to avoid aliasing. For example, the concentrations are determined every 20 msec (scanning rate of 50 Hz). In an exemplary embodiment, the fastest changes to be expected take place over a period of 100 msec (300 msec in case of CO2), so that no aliasing is to be expected in case of the selected scanning rate. In addition, different sensors for the different gases can be used, which are preferably arranged in the immediate vicinity of one another, in order to keep time delays (because of the propagation velocity) low during the measurements of the concentrations and to obtain measured values synchronized in time, Spaced-apart sensors can be used in other exemplary embodiments, wherein the spaces based on the propagation velocity of the gas can be taken into consideration in the measurements.

Figure 3:
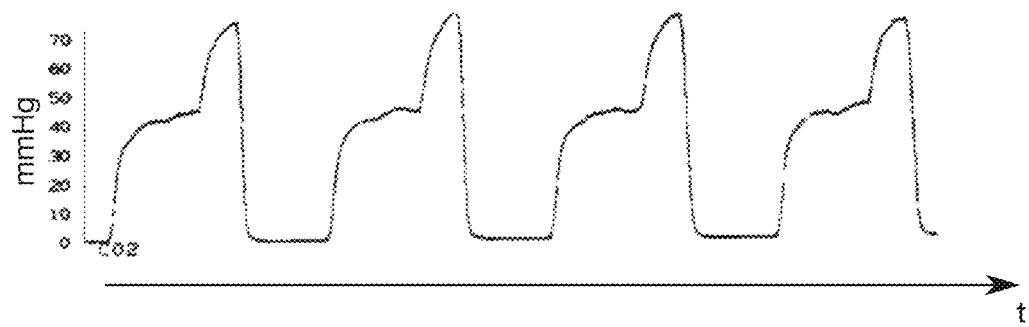
FIG. 3 is a graph showing a capnogram in an exemplary embodiment.

In the exemplary embodiment shown in FIG. 2, for example, a continuous monitoring of the suctioning measurement can be ensured in case of maximum availability of the gas measurement. In general, in exemplary embodiments, the process 10 can therefore also comprise a suction of the breathing gas mixture via a sample gas line 52. In some exemplary embodiments, anomalous time curves of the CO2 concentration may be the basis for the detection of a leak. FIG. 3 shows a capnogram of a patient in an exemplary embodiment (time curve of CO2 concentration in mmHg). The capnogram was recorded in a system with an internal gas analysis sensor. The curve shows a periodic curve, which at first rises to a plateau within a period. The plateau is followed by a brief rise before the concentration drops abruptly to zero. In this investigation, the CO2 concentrations correlated well with the arterial carbon dioxide partial pressure. Therein the highest CO2 concentrations were more than 30 mmHg above the highest values of the arterial carbon dioxide partial pressure, cf. also "End-Tidal CO2 Excretion Waveform and Error with Gas Sampling Line Leak," Zupan, Joanne MD; Martin, Michael MD; Benumof, Jonathan L. MD, *Anesthesia & Analgesia*: June 1988, volume 67, issue 6, pp. 579-581.

Figure 4:
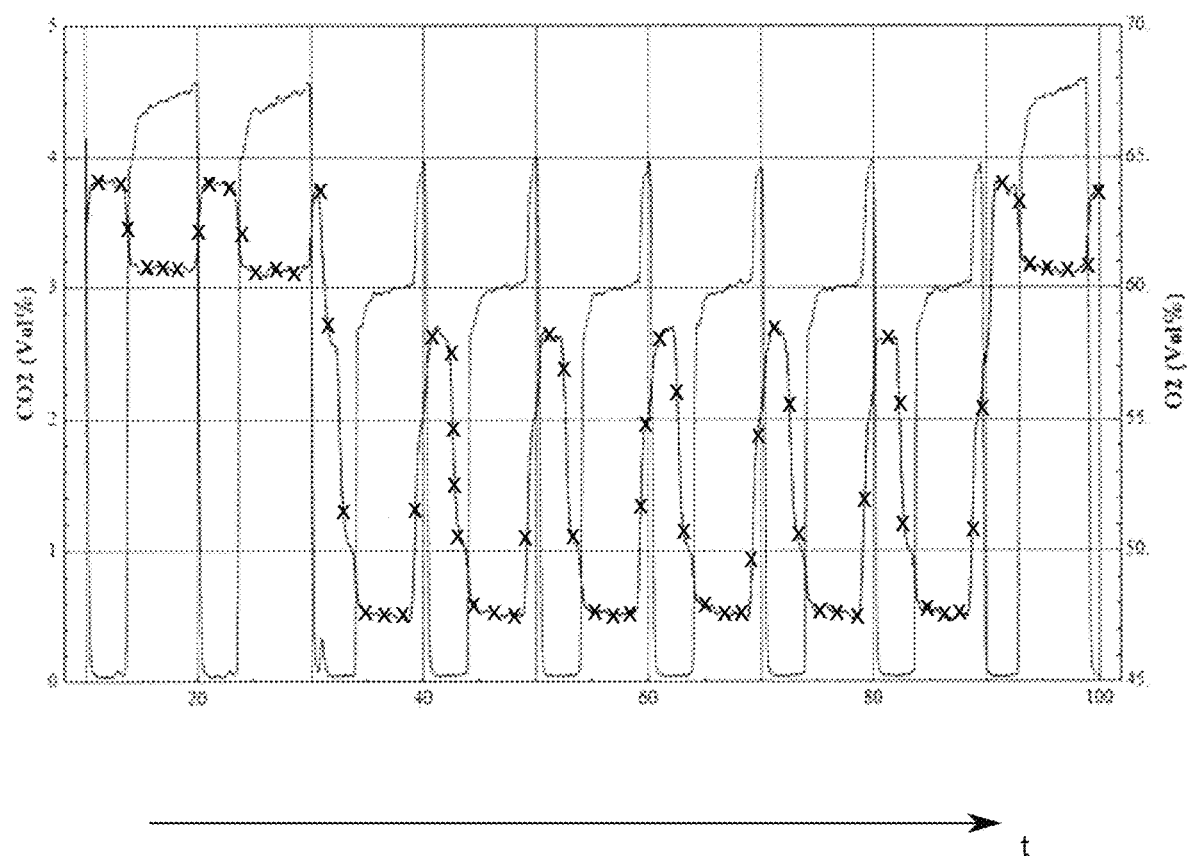
FIG. 4 is a graph showing concentration curves of carbon dioxide and oxygen in an exemplary embodiment.

Similar anomalies are also found in capnograms which were generated in the laboratory with a simulation lung (e.g., Michigan lung) in the following exemplary embodiment. FIG. 4 shows concentration curves of carbon dioxide (unidentified curve in volume percent) and oxygen (curve identified by "x" in volume percent) in an exemplary embodiment. In this case, a small leak was opened in the area of the sample gas inlet/water trap, cf. FIG. 2, at the patient gas module as of T=30 sec and closed at T=90 sec (pierced sample gas tube). The O2 curve is shown simultaneously with the CO2 curve as well. In addition to the peak-isle overshooting of the CO2 curve in case of a leak at the end of each phase of exhalation discussed in the aforementioned publication, an effect on the O2 curve also takes place simultaneously as a result of the dilution due to the leak. In addition to a change in the amplitude values and mean values of the concentration curves, which are not leak-specific, however, an apparent phase shift between the CO2 curve and the O2 curve is found, however. E.g., changes in the ventilation settings and fresh gas concentration are also critical for the amplitude and mean values of the concentration curves.

The phase shift between the CO2 curve and the O2 curve that can be observed in case of a leak (present depending on concentration conditions and/or even between CO2 curve and Agas or N2O curve) is absolutely applicable in terms of measuring, i.e., without knowledge of the concentration conditions of the previous breathing phases. This may be advantageous since leaks can be detected in a reliable manner with this feature even in case of changing concentration conditions and without prior knowledge of or without measured values of past breathing phases. As another advantage, the process being described makes it possible to detect leaks even if they do not occur abruptly over time, but rather grow continuously over a plurality of breathing phases. A prerequisite for this process is for sufficiently major ventilation pressure changes to be present at the connection point of the sample gas line at the patient ($\Delta P \geq 10$ hPa). In exemplary embodiments, a phase shift between the first curve (CO2) and second curve (e.g., O2) can accordingly be used as similarity indicator. The determination 16 of the similarity indicator may comprise the determination of a deformation in the first curve or in the second curve, which deformation is peculiar to a leak, cf FIGS. 3 and 4. In addition, the similarity indicator may be an indicator of a symmetry between the first curve and the second curve.

A quantitative analysis of the concentration curves can accordingly take place in some exemplary embodiments. In this case, ventilation pressure fluctuations, which lead to phase shifts between CO2 curve and O2 or Agas curve/N2O curve, may form a basis. These phase shifts are analyzed in the exemplary embodiments described below by means of the covariance (Coy):

$$Cov_{xy} := \frac{2}{n} \sum_{i=1}^{n} \left[ \frac{(x_i - \bar{x})}{Max_x - Min_x} \times \frac{(y_i - \bar{y})}{Max_y - Min_y} \right]$$

with the maximum (Max) and the minimum (Min) of the concentration values within the breathing phase being considered and with the mean values $$\bar{x} = \frac{1}{n} \sum_{i=1}^{n} x_i,$$

$$\bar{y} = \frac{1}{n} \sum_{i=1}^{n} y_i.$$

Here, the running index i is beyond all values in the breathing phase being considered (i=1 . . . n). The values $x_i$ denote the real time CO2 values and the values $y_i$ denote the real time values from the group O2, Agas or N2O. Thus, there is at least one analysis per breathing phase in the exemplary embodiments. In case of no leak, ideally $$Cov(CO2,Y) = -\text{mit } Y \in (O_2, AGas, N_2O),$$

is valid, i.e., the standardized and mean-value-exempt curves are (at least theoretically) completely antisymmetric Actually, the corresponding covariance values are, however, rather between −0.6 and −0.8. The similarity indicator is accordingly in the present exemplary embodiment a covariance between the first (CO2) time curve and the second (O2) time curve of the concentrations. Hence, in exemplary embodiments, the similarity indicator may be an indicator of symmetry or asymmetry present between the curves as well. In case of a leak, there is a ventilation-pressure-caused phase shift, which shifts the covariance in the direction of positive values. The threshold value for the covariance for the detection of a leak is, e.g., −0.4, i.e., $$Cov_{xy} > -0.4 \Rightarrow \text{leak}\exists$$

In general, the threshold value is dependent on the state of construction of the patient gas module, etc. Hence, the threshold value does not represent a universal variable, but rather is in at least some exemplary embodiments specific to the patient gas module used. In this exemplary embodiment, the process thus further comprises the comparison of the similarity indicator with a threshold value and the detection of the leak based on the threshold value comparison.

In some other exemplary embodiments, an improved distinction between leak and non-leak can be achieved, e.g., by the integrity of the suction section being determined at a fixed time with an independent process (for example, with a pressure test as described further below). The actual covariance value can then be determined, or the limit value for a leak can be adapted to this measured value (e.g., limit value=⅔×covariance mean value in case of no leak). In this respect, the process 10 can further comprise the calibration of the threshold value based on a reference measurement at the ventilation system without leak in some exemplary embodiments.

Figure 5:
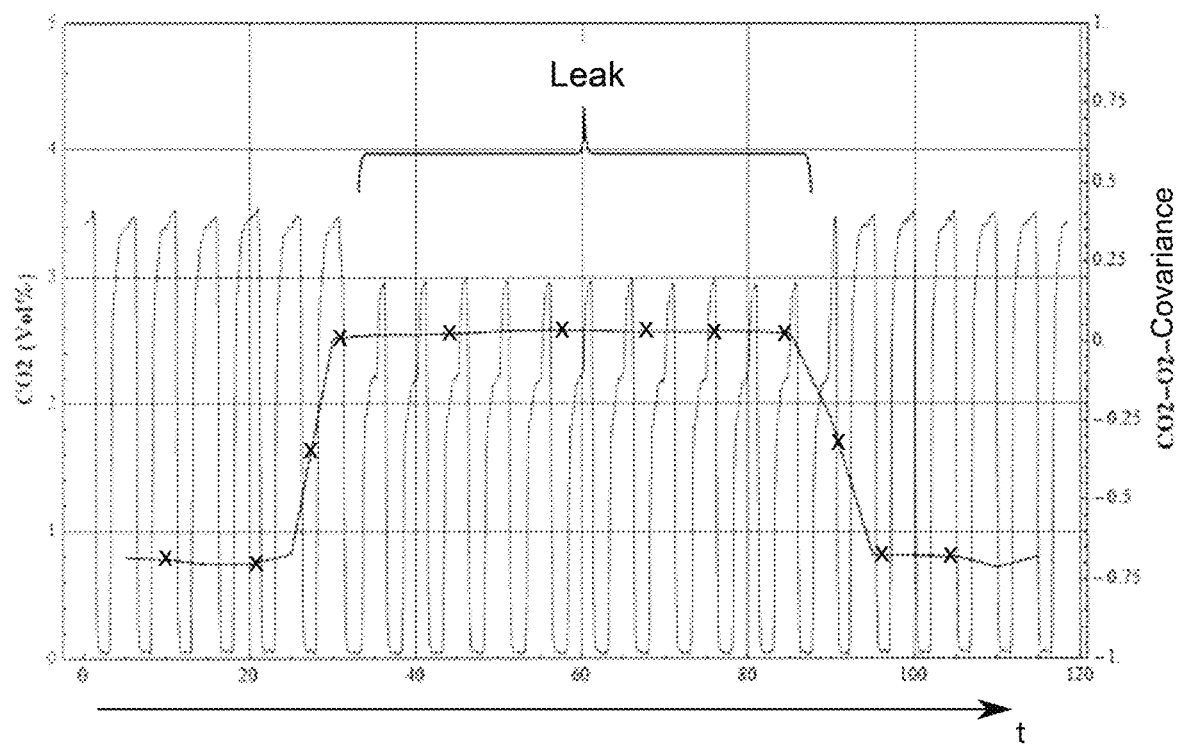
FIG. 5 is a graph showing a carbon dioxide concentration curve and a carbon dioxide-oxygen covariance curve in an exemplary embodiment.

FIG. 5 shows a carbon dioxide concentration curve (curve without markings) and a carbon dioxide-oxygen covariance curve (curve identified by "x") in an exemplary embodiment for the detection of a leak with the process described above and in the system shown in FIG. 2. The CO2 concentration and the CO2/O2 covariance without leak and with leak (perforation of the suction tube in the area of the water trap) can be seen in FIG. 5. The leak was opened at t 30 sec and closed again at t 90 sec. The curve of the covariance (identified by "x") records a marked jump when the leak is open and is hence suitable for detecting the leak.

In another exemplary embodiment, concentration changes instead of concentrations are considered directly in order to determine the similarity indicator. The similarity indicator may then be a covariance between a first time curve and a second time curve of concentration changes. Similar to the above-mentioned case (concentration covariance), the detection of a leak is likewise based on the covariance in the present exemplary embodiment; however, the change (or the differences) in the real time measured values are taken into consideration here. It may be advantageous here that significant changes then emerge markedly even at low ventilation frequencies and the unchanged parts of the time curves are better suppressed or not analyzed.

$$\Delta Cov_{xy} := \frac{2}{n-l} \sum_{i=1+l}^{n} [(\tilde{x}_i - \tilde{x}_{i-1}) \cdot (\tilde{y}_i - \tilde{y}_{i-1})]$$

with the standardized values $$\tilde{x}_i = \frac{1}{\text{Max}_x - \text{Min}_x}\left[x_i - \frac{\text{Max}_x - \text{Min}_x}{2}\right],$$

$$\tilde{y}_i = \frac{1}{\text{Max}_y - \text{Min}_y}\left[y_i - \frac{\text{Max}_y - \text{Min}_y}{2}\right]$$

is thus obtained as delta covariance.

E.g., l=10 turned out to be a useful value (at a scanning rate of ½0 msec obtained therefrom as time difference 200 msec for the mean value differences). As in the case of the covariance, the sum is always analyzed, for example, over the current breathing phase and then one value per breathing phase is obtained in each case. A limit value can initially be determined (calibration) for distinction between leak and non-leak here as well. In this respect, the process 10 may also further comprise in this exemplary embodiment the comparison of the similarity indicator with a threshold value and the detection of the leak based on the threshold value comparison. In addition, the calibration of the threshold value may take place based on a reference measurement at the ventilation system without leak.

The determination of a run time of the breathing gas mixture from the patient via a sample gas line 52 to a patient gas nodule 50 takes place in the process in another exemplary embodiment. The process 10 further comprises a determination of a run time of concentration changes in the breathing gas mixture and the determination of the similarity indicator based on the run times. A gas stream is suctioned from the patient in case of the suctioning patient gas measurement, cf. FIG. 2. The concentrations of the gas mixture of the gas stream are analyzed by the gas measurement. The gas mixture usually consists of an oxygen component $\sigma_{O2}$, a CO2 component $\sigma_{CO2}$, an anesthetic gas component $\sigma_A$ and a nitrous oxide component $\sigma_{N2O}$. If the gas mixture has the concentration values $a\sigma_i$ at the time t, these values are detected by the gas measurement at a time $t+\Delta t_{pat}$. The cause of the delay is the run time $\Delta t_{pat}$, which the gas needs to reach the patient gas module from the patient via the sample gas line. The run time may be approximately determined in the form $$\Delta t_{pat} = \frac{L_{sample} \cdot \pi \cdot d_{sample}^2}{4 \cdot \dot{V}_{gas}}$$

The suctioned gas stream $\dot{V}_{gas}$ needs the time $\Delta t_{pat}$ in order to reach the patient gas module from the patient via the sample gas line with the length $L_{sample}$ and with the cross section $\pi \cdot d_{sample}^2$.

The pressure at the patient is likewise detected by the patient gas module. However, the measured pressure value does not reflect the conditions at the patient due to the volumes and flow resistances located between the patient and the patient gas module. Only the pressure difference between the breathing phases inhalation and exhalation can be reflected approximately correctly. In addition, pressure fluctuations can be detected at the patient by the patient gas module almost at the same time since the pressure signal propagates at the speed of sound.

Figure 6:
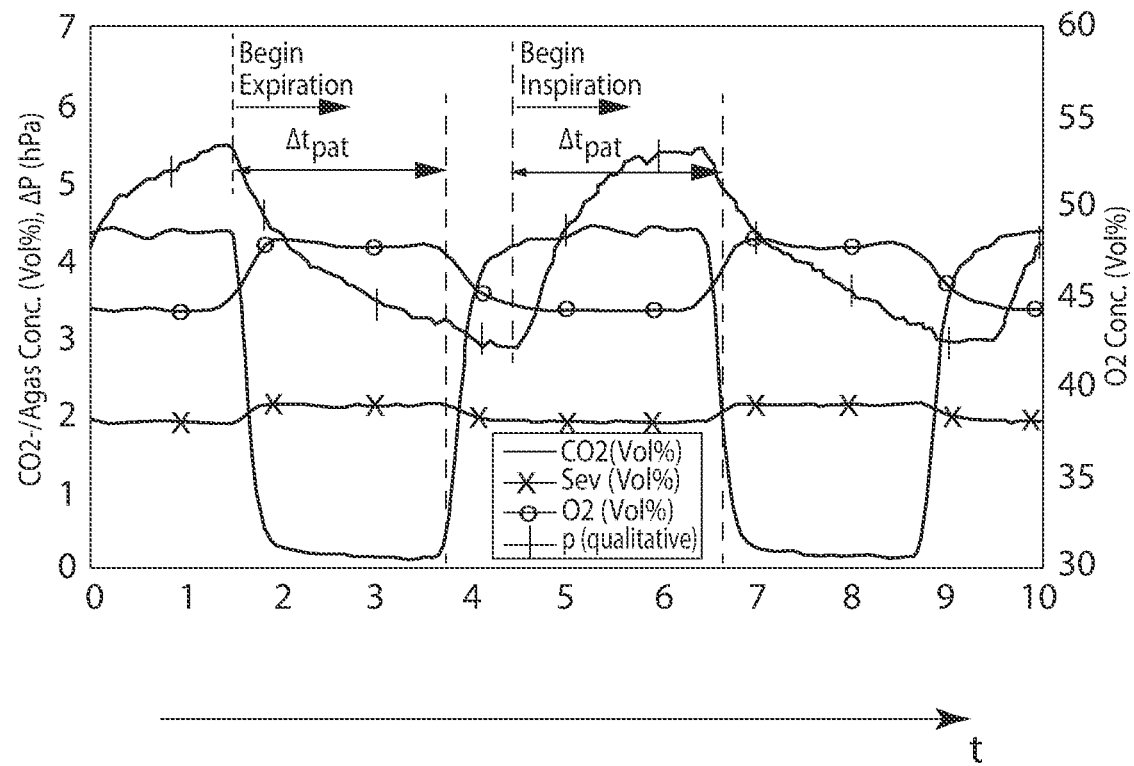
FIG. 6 is a graph showing concentration curves and pressure curves in a patient gas module in an exemplary embodiment without leak.

FIG. 6 shows concentration curves and pressure curves in a patient gas module in an exemplary embodiment without leak. FIG. 6 illustrates measured concentrations of CO2 (without marking), nitrous oxide (sevoflurane with "x" marking), O2 (with "o" marking) as well as a qualitative curve of the pressure p (with "|" marking) in the patient gas module as a function of time without a leak.

At the beginning of a phase of exhalation the pressure signal drops in the patient gas module, since the airway pressure drops to the exhalation pressure. At the beginning of a phase of inhalation, the pressure signal rises in the patient gas module, since the airway pressure rises to the inhalation pressure. These two times are marked correspondingly in FIG. 6. The CO2 signal rises in a time-delayed manner (by $\Delta t_{pat}$) at the beginning of a phase of exhalation and the signals for O2 and sevoflurane drop correspondingly. At the beginning of a phase of inhalation, the CO2 signal drops in a time-delayed manner ($\Delta t_{pat}$) and the signals for O2 and sevoflurane rise correspondingly. These transitions are also marked in FIG. 6. The time delay $\Delta t_{pat}$ can be easily seen and has the value $\Delta t_{pat}$ 2.3 sec. The pneumatic time delay is likely to drop markedly lower since a delay in the processing of the concentration signals is likewise contained in the signal curve.

It can be clearly seen that in the case of a breathing phase change the pressure signal clearly reacts to the change before the concentration signals. This and the fact that no further significant changes in the concentration curves occur are indicative of a system without leak. In case no relevant leak has an effect on the patient gas measurement, any change in the concentrations of the gas mixture at the patient, which are brought about by the breathing phases, can be detected after the time $\Delta t_{pat}$ at the earliest.

In case a relevant leak is present in the area of the patient gas measurement, the flow-mechanical properties of the system are changed. If, e.g., a leak is observed at the location, where the sample gas line 52 is connected to the patient gas module 50, cf. FIG. 2, a volume flow $\dot{V}_{leak}$ is obtained, which penetrates into the system as a function of the present pressure difference $\Delta p_{leak}$ and changes the concentrations of the gas mixture to be measured, or is released from the system, but does not change the composition of the gas mixture. In case a volume flow $\dot{V}_{leak}$ enters the system, a volume flow $\dot{V}_{pump}$, which the pump suctions in the patient gas module, is composed of a component $\dot{V}_{sample}$, which flows through the sample gas line, and $\dot{V}_{leak}$. The two components vary depending on the breathing phase. If the pressure at the patient is high in the phase of inhalation, the pressure difference at the location of the leak is small, whereas in the phase of exhalation the pressure at the patient is low and thus the pressure difference at the location of the leak is large. These pressure fluctuations change the volume flow $\dot{V}_{leak}$ and thus the concentrations of the gases at the location of the leak as well.

These changes are detected by the patient gas module 50 with a different time delay than the changes at the patient. A change in the gas mixture at the location of the leak can be detected by the patient gas module after the time $$\Delta t_{leak} = \frac{\Delta L_{sample} \cdot \pi \cdot d_{sample}^2}{4 \cdot \dot{V}_{gas}}$$

In this case, $\Delta L_{sample}$ designates here the distance between the peak location (e.g., at the inlet of the water trap) up to the patient gas sensor and $\Delta L_{sample} < L_{sample}$ shall apply.

Figure 7:
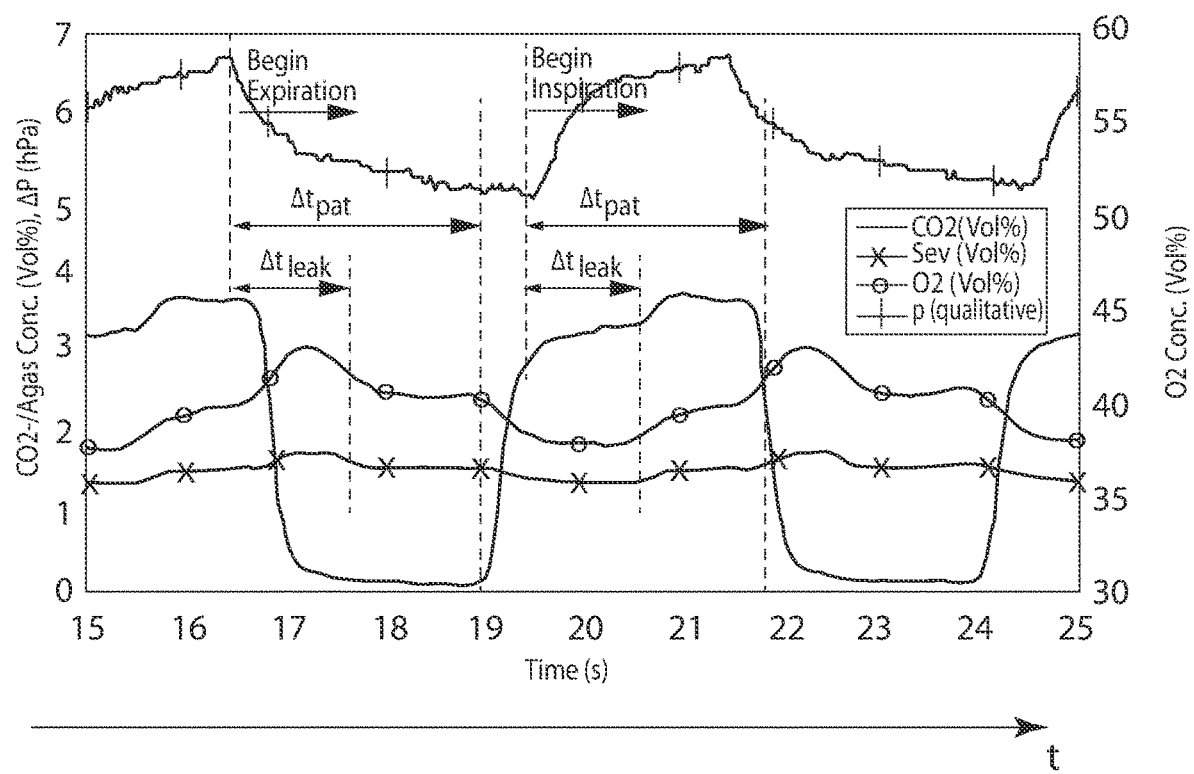
FIG. 7 is a graph showing concentration curves and pressure curves in a patient gas module in an exemplary embodiment with leak.

FIG. 7 shows concentration curves and pressure curves in a patient gas module in an exemplary embodiment with leak. FIG. 7 shows measured concentrations of CO2 (without marking), sevoflurane ("x" marking), O2 ("o" marking) and the qualitative curve of the pressure p ("|" marking) in the patient gas module 50 as a function of the time with a leak. Other anomalies arise in case of a leak in addition to the curves of the concentration signals, which curves are explained on the basis of FIG. 6. The concentrations of O2 and sevoflurane drop after a time $\Delta t_{leak}$ in relation to the start of the phase of exhalation. This is a consequence of the increased pressure difference at the location of the leak in the phase of exhalation and of the greater dilution of the suctioned gas connected therewith due to the increased, penetrating volume flow.

The CO2 signal rises, after a time $\Delta t_{leak}$ in relation to the start of the phase of inhalation, and the O2 and sevoflurane concentrations drop at the same time. This is a consequence of the ventilation-pressure-related reduced pressure difference at the location of the leak in the phase of inhalation and of the lower dilution of the suctioned gas connected therewith due to the reduced, penetrating volume flow. In this case, the value $\Delta t_{pat} \approx 2.3$ sec is obtained again, but also the markedly smaller value $\Delta t_{leak} \approx 1.2$ sec.

If a relevant leak has an effect on the patient gas measurement, any change in the concentrations of the gas mixture at the patient, which is related to a pressure change due to a change in the breathing phases, leads to measured concentration changes after a delay of $\Delta t_{leak}$ and $\Delta t_p$, wherein $\Delta t_{leak} < \Delta t_{pat}$ applies.

The indicator of the determination of a leak is the behavior of the concentration signals at the patient gas module after the beginning of a breathing phase. Changes in the concentrations, which occur only after $\Delta t_{pat}$, denote a system without leak, and changes that occur already after $\Delta t_{leak}$ indicate a system with leak.

In exemplary embodiments with this type of detection of a leak, an indicator of the beginning of the breathing phases and an indicator of the detection of the times of the concentration changes at the patient gas module 50 can be determined. Indicators of the beginning of the breathing phases are, for example, the pressure signal in the patient gas module (see FIGS. 6 and 7) or a signal from the breathing system, which indicates the beginning of a breathing phase.

Indicators of the detection of the time of a concentration change are a significant change in the first derivation of the concentration values as a function of time or an analysis of the concentration values before and after the beginning of the breathing phase.

The process 10 described above makes it possible to detect a leak in a suctioning patient gas measurement due to the detection of the time delay of concentration changes in the suctioned gas mixture after a change in the breathing phase. Exemplary embodiments may accordingly comprise the determination of the run time based on concentration changes over time or based on an analysis of concentration changes before and after a beginning of breathing phases. The similarity indicator may accordingly be determined by a time delay or correspond to a time delay.

In another exemplary embodiment, the process 10 further comprises the carrying out of a pressure measurement at the ventilation system when a leak was detected. If a leak indication is now given by an aforementioned process, then a pressure measurement operation is carried out in at least some exemplary embodiments, which then makes possible a valid statement about the leak status. The procedure of the operation, which may take place at any desired time during a ventilation surgery and the variation of the measured pressure in the gas monitor (or in the measuring cell of the gas monitor) because of the pronounced ventilation pressure fluctuations, is divided according to: switching off of the sample gas pump, 1. outlet-side sealing of the patient gas module (by means of a corresponding electromagnetic valve),
2. determination of the inhalation pressure and the exhalation pressure in the patient gas module,
3. calculation of the pressure difference between exhalation pressure value and inhalation pressure value in the patient gas module, and
4. comparison with the pressure values in the closed ventilation circuit or with the set values at the ventilator: In case of a difference>3 hPa, a leak alarm is generated.
5. It can be ensured by this procedure in some exemplary embodiments that the frequency of this operation, which is connected to the failure of the gas-measuring function, is as low as possible and is carried out only if there is a substantiated leak suspicion. At the same time, an alarm generation can also be triggered only if a unambiguous leak is present.

Figure 8:
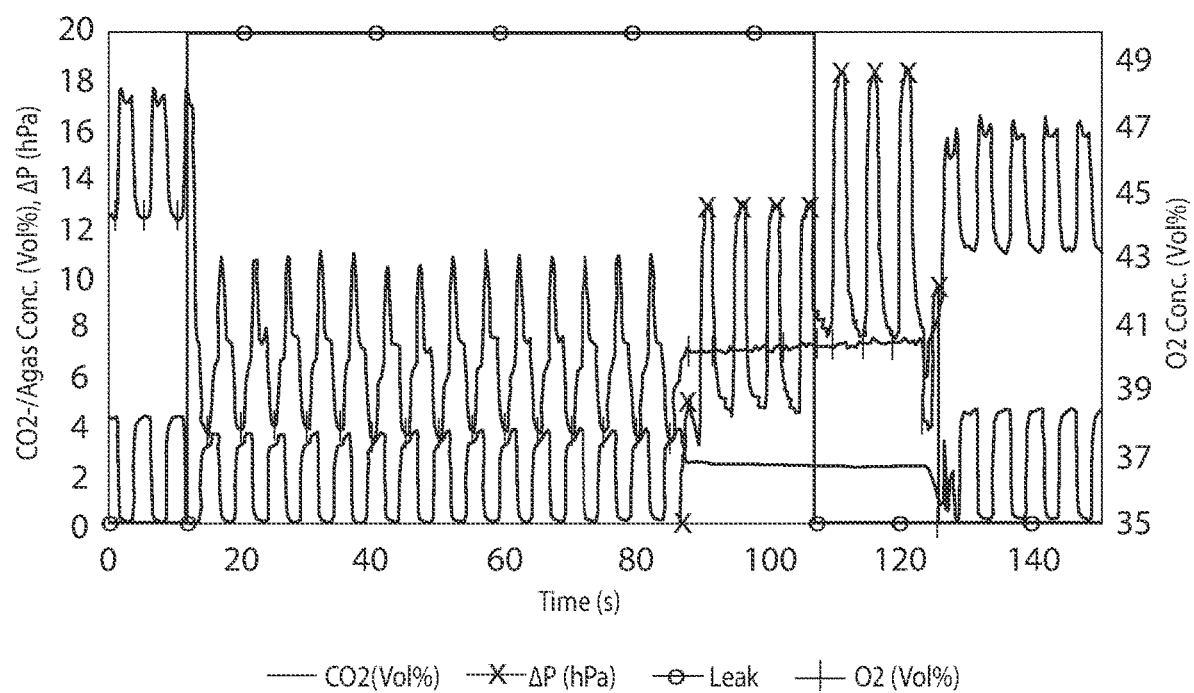
FIG. 8 is a graph showing concentration curves and pressure curves in, a patient gas module in another exemplary embodiment with leak.

FIG. 8 shows concentration curves and pressure curves in a patient gas module 50 in another exemplary embodiment with leak. FIG. 8 shows curves for CO2 (without marking), O2 (with "|" marking), the leak section (with "o" marking) and the pressure curve $\Delta P$ (pressure in the patient gas module in relation to the ambient pressure, with "x" marking) with and without leak. The pressure operation with switched-off sample gas pump is identified by constant O2 and CO2 curves. The pressure operation with leak (time range t≈90 sec ... 100 sec) and without leak (time range t≈105 sec ... 125 sec) was carried out for better representation of the significance of this test. The differences can be clearly seen in FIG. 8.

The features disclosed in the above description, in the claims and in the drawings may be significant both individually and in any desired combination for the embodiment of exemplary embodiments in the different configurations thereof and, unless the description shows something different, they may be combined with one another as described.

Even though some aspects were described in connection with a device, it is obvious that these aspects also represent a description of the corresponding process, so that a block or a component of a device can also be defined as a corresponding process step or as a feature of a process step. Analogously to this, aspects that were described in connection with or as a process step also represent a description of a corresponding block or detail or feature of a corresponding device.

Depending on certain implementation requirements, exemplary embodiments of the present invention may be implemented in hardware or in software. The implementation may be carried out with the use of a digital storage medium, for example, a floppy disk, a DVD, a Blu-Ray disk, a CD, a ROM, a PROM, an EPROM, an EEPROM or a FLASH memory, a hard drive or another magnetic or optical memory, on which electronically readable control signals are stored, which can or do interact with a programmable hardware component such that the process in question will be executed.

A programmable hardware component may be formed by a processor, a computer processor (CPU=Central Processing Unit), a graphics processor (GPU=Graphics Processing Unit), a computer, a computer system, an application-specific integrated circuit (ASIC), an integrated circuit (IC), a system on chip (SOC), a programmable logic element or a field-programmable gate array with a microprocessor (FPGA).

The digital storage medium may therefore be machine- or computer-readable. Some exemplary embodiments consequently comprise a data storage medium, which has electronically readable control signals, which are capable of interacting with a programmable computer system or with a programmable hardware component such that one of the processes described here will be executed. An exemplary embodiment is thus a data storage medium (or a digital storage medium or a computer-readable medium), on which the program for executing one of the processes described here is recorded. Exemplary embodiments of the present invention may generally be implemented as a program, firmware, computer program or computer program product with a program code or as data, wherein the program code or the data act such as to execute one of the processes when the program is running on a processor or on a programmable hardware component. The program code or the data may also be stored, for example, on a machine-readable medium or data storage medium. The program code or the data may be present, among other things, as source code, machine code or byte code as well as as other intermediate code.

Another exemplary embodiment is, further, a data stream, a signal sequence or a sequence of signals, which data stream or sequence represents or represent the program for executing one of the processes being described here. The data stream, the signal sequence or the sequence of signals may be configured, for example, such as to be transferred via a data communication connection, for example, via the Internet or another network. Exemplary embodiments are consequently also signal sequences representing data, which are suitable for a transmission via a network or a data communication connection, wherein the data represent the program.

A program according to an exemplary embodiment may implement one of the processes during its execution, for example, by this reading storage locations or by writing a datum or a plurality of data into these, whereby switching operations or other processes are possibly elicited in transistor structures, in amplifier structures or in other electrical, optical, magnetic components or in components operating according to another principle of function. Data, values, sensor values or other pieces of information may correspondingly be captured, determined or measured by a program by reading a storage location. A program may therefore capture, determine or measure variables, values, measured variables and other pieces of information by reading one or more storage locations as well as bring about, prompt or execute an action as well as actuate other devices, machines and components by writing into one or more storage locations.

The above-described exemplary embodiments represent merely an illustration of the principles of the present invention. It is obvious that modifications and variations of the arrangements and details being described here may be clear to other persons killed in the art. It is therefore intended that the present invention be limited only by the scope of protection of the following patent claims rather than by the specific details, which were presented here on the basis of the description and the explanation of the exemplary embodiments.

While specific embodiments of the invention have been shown and described in detail to illustrate the application of the principles of the invention, it will be understood that the invention may be embodied otherwise without departing from such principles.

The invention claimed is:

1. A process for the detection of a leak in a patient gas module, which suctions and analyzes a continuous sample gas stream from a ventilated patient, the process comprising the steps of:
   determining a first time curve of a carbon dioxide concentration in a breathing gas mixture of the patient;
   determining a second time curve of a concentration of an other gas in the breathing gas mixture, which other gas is different from carbon dioxide;
   determining a statistical similarity indicator between the first time curve and the second time curve; and
   detecting the leak based on a change of the similarity indicator, wherein the similarity indicator measures a phase shift between the first curve and the second curve.

2. A process in accordance with claim 1, wherein the other gas is oxygen, nitrous oxide or an anesthetic gas.

3. A process in accordance with claim 1, wherein the determination of the similarity indicator comprises determining a deformation in the first curve or in the second curve, which determined deformation is peculiar to a leak.

4. A process in accordance with claim 1, wherein the similarity indicator is an indicator of a symmetry between the first curve and the second curve.

5. A process in accordance with claim 1, wherein the similarity indicator is a covariance between the first time curve and the second time curve of the concentrations.

6. A process in accordance with claim 1, wherein the similarity indicator is a covariance between concentration changes of the first time curve and the second time curve.

7. A process in accordance with claim 1, further comprising the step of comparing the similarity indicator with a threshold value, wherein the detection of the leak is based on the threshold value comparison.

8. process in accordance with claim 7, further comprising a calibration of the threshold value based on a reference measurement at the ventilation system without a leak.

9. A process in accordance with claim 1, further comprising the step of determining a run time of the breathing gas mixture from the patient via a sample gas line to a patient gas module.

10. A process in accordance with claim 9, further comprising the step of:
    determining a run time of concentration changes in the breathing gas mixture; and
    determining a similarity indicator based on the run times.

11. A process in accordance with claim 10, further comprising the step of determining the run time based on concentration changes over time or based on an analysis of concentration changes before and after the beginning of breathing phases.

12. A process in accordance with claim 1, further comprising the step of carrying out a pressure measurement at the ventilation system when a leak was detected.

13. A process in accordance with claim 1, further comprising the steps of:
    providing a program code for carrying out at least one of the steps of determining the first time curve, determining the second time curve, determining the statistical similarity indicator and detecting the leak; and
    executing the program code on a computer, on a processor or on a programmable hardware component.

14. A device for detecting a leak in a patient gas module, which the patient module suctions and analyzes a continuous sample gas stream from a ventilated patient, the device comprising:
- a signal connection for receiving data of carbon dioxide concentration in a breathing gas mixture of the patient and receiving data of an other gas concentration in the breathing gas mixture, which other gas is different from carbon dioxide; and
- a processor connected to the signal connection and configured to:
  - determine a first time curve of a carbon dioxide concentration in a breathing gas mixture of the patient from the received data of carbon dioxide concentration;
  - determine a second time curve of a concentration of the other gas in the breathing gas mixture gas of the patient from the received data of the other gas concentration;
  - determine a statistical similarity indicator between the first time curve and the second time curve; and
  - detect the leak based on a change of the similarity indicator, wherein the similarity indicator measures a phase shift between the first curve and the second curve.

15. A device in accordance with claim 14, wherein the other gas is oxygen, nitrous oxide or an anesthetic gas.

16. A device in accordance with claim 14, wherein the processor is further configured to compare the similarity indicator with a threshold value, wherein the detection of the leak is based on the threshold value comparison.

17. A device in accordance with claim 14, wherein the similarity indicator is a covariance between the first time curve and the second time curve of the concentrations.

18. A device in accordance with claim 14, wherein the processor is further configured to determine a run time of the breathing gas mixture from the patient to a patient gas module, via a sample gas line.

19. A ventilation system comprising:
- a ventilation arrangement with a patient connection for ventilating the patient;
- a patient gas module configured to suction and analyzes a continuous sample gas stream from the patient connection and to output data of carbon dioxide concentration in a breathing gas mixture of the patient and data of an other gas concentration in the breathing gas mixture of the patient, which other gas is different from carbon dioxide; and
- a device for detecting a leak in a patient gas module, the device comprising:
  - a signal connection for receiving data of carbon dioxide concentration in a breathing gas mixture of the patient and receiving data of another gas concentration in the breathing gas mixture, which other gas is different from carbon dioxide; and
  - a processor connected to the signal connection and configured to:
  - determine a first time curve of a carbon dioxide concentration in a breathing gas mixture of the patient from the received data of carbon dioxide concentration;
  - determine a second time curve of a concentration of the other gas in the breathing gas mixture gas of the patient from the received data of the other gas concentration;
  - determine a statistical similarity indicator between the first time curve and the second time curve; and
  - detect the leak based on a change of the similarity indicator, wherein the similarity indicator measures a phase shift between the first curve and the second curve.

20. A ventilation system in accordance with claim 19, wherein the other gas is oxygen, nitrous oxide or an anesthetic gas.

* * * * *